United States Patent [19]

Pourrat et al.

[11] 4,033,818

[45] July 5, 1977

[54] PROCESS FOR THE PREPARATION OF A COMPLETE EXTRACT OF PILEWORT ROOTS

[75] Inventors: Henri Pourrat; Aimée Pourrat nee Gaillard, both of Clermont Ferrand Cedex, France

[73] Assignee: Centre Europeen de Recherches Mauvernay C.E.R.M., Riom, France

[22] Filed: July 15, 1976

[21] Appl. No.: 705,460

[30] Foreign Application Priority Data

July 18, 1975 France .............................. 75.22527

[52] U.S. Cl. .................................... 195/7; 195/32;
    424/195; 260/236.5
[51] Int. Cl.² ............................................. C12D 1/00
[58] Field of Search ............................ 195/2, 32, 7

[56] References Cited

UNITED STATES PATENTS

| 2,774,713 | 12/1956 | Gould et al. | 195/32 |
| 3,620,919 | 11/1971 | Hardman | 195/7 |

OTHER PUBLICATIONS

Chemical Abstracts, 128703q vol. 71, (1969).

*Primary Examiner*—Alvin E. Tanenholtz

[57] ABSTRACT

The invention provides a process for the preparation of a complete extract of pilewort roots, used in cosmetological compositions, which consists of first subjecting the dried and ground roots to an extraction with 35°–45° C petroleum ether and then treating the insoluble powder by extraction with an aqueous lower alcohol. After having removed the insoluble impurities by filtration, the filtrate is treated with papaine and is concentrated to a solids content of 40 to 50%. Aqueous alcohol is then added to the concentrated extract and the deposit thus formed is removed by decantation when cold, leaving the desired extract.

5 Claims, No Drawings

PROCESS FOR THE PREPARATION OF A COMPLETE EXTRACT OF PILEWORT ROOTS

The present invention relates to a process for the extraction of the active substances contained in the tuberised roots of pilewort (*Ficaria ranunculoides*), to the extract thus obtained and to its application in cosmetology, in particular in products such as creams, skin lotions and make-up.

The virtues of pilewort root in the treatment of haemorrhoidal venous dilations have been known for a long time, and recently developed processes have made it possible to isolate — after the pilewort tubercles have been stabilised by means of alcohol vapours — the active principle, (namely the saponins) which is responsible for the therapeutic activity of the product.

The main object of the invention is to provide a process for the selective extraction of pilewort roots which makes it possible to remove the vegetable debris and other compounds which are detrimental to the preservation of the extract or can cause irritation in the cosmetological applications envisaged, while retaining all the active substances contained in the plant. These active substances consist of the saponins as mentioned above, and also phenolic compounds and glycosides of flavone derivatives.

The combination of these active substances imparts softening and soothing properties to the cosmetic preparations which contain the extract obtained by the process of the invention, whilst also improving the physical appearance of the skin.

This process consists fundamentally of subjecting the dried pilewort roots, which have not been subjected to any previous stabilisation by means of alcohol vapours, to a succession of extractions using certain specified solvents.

More specifically, the present invention provides a process for the extraction of the active substances from tuberised pilewort roots, said process comprising the following stages:

a. macerating the pilewort roots, which have previously been dried and ground to a powder, in 35°–45° C petroleum ether, extracting them with this solvent, so as to remove all the substances soluble therein separating the resulting solid residue from the solvent and drying it;

b. macerating the dried residue in an aqueous lower alcohol and extracting it with a supplementary amount of this aqueous alcohol;

c. subjecting the resulting alcoholic extract to two successive concentrations in each of which the quantity of alcohol is approximately halved, allowing the extract to cool after each concentration, and removing precipitated impurities by filtration;

d. treating the filtrate with papaine and concentrating it to a solids content of 40 to 50%;

e. adding an equal volume of an aqueous lower alcohol to the viscous solution thus obtained, allowing the mixture to stand in the cold, and removing the insoluble products by decantation, filtration or centrifugation; and f. distilling off the alcohol so as to give an aqueous extract.

In the first stage, the pilewort roots, dried and ground to a powder, are macerated for several hours in 35°–45° C petroleum ether (i.e. the fraction while distils between 35° and 45° C); after having added a fresh amount of solvent, an extraction is carried out in a percolator, such as a Soxhlet, which removes all the substances soluble in this solvent (pigments, free triterpene genins and various organic acids), and the powder is then isolated and dried so as to remove the last traces of solvent.

In the second stage, the powder is brought into contact with an aqueous lower alcohol, for example methanol or ethanol of 70° to 50° strength, so as to dissolve the active substances contained in the powder. After having macerated the material for about one day, a fresh amount of aqueous alcohol is added and the extraction is carried out. The alcoholic extract thus obtained is then subjected to two successive concentrations which each time lower the alcoholic strength by about half and make it possible, on cooling, to precipitate impurities consisting essentially of viscous products of the mucilage type, and of proteins. These impurities are removed by filtration in accordance with the conventional processes, preferably with the addition of a filtration adjuvant.

In the last stage, the extract, which still contains, in amounts which vary but are always small, suspended proteins, which would interfere with the preservation of the extract, is treated with papaine which, as is known, causes a scission of the peptide chains. After having added the papaine, preferably in an amount of about 1 g per liter of extract obtained from the preceding stage, and having allowed the reaction to take place for several hours, the extract is concentrated until the solids content is between 40 and 50%.

A volume of alcohol preferably equal to that used in the second stage, but of a higher strength, is added to the viscous solution thus obtained. The solution is preferably then left at least 24 hours in the cold, and the insoluble products are removed by decanting or by any other process such as filtering or centrifuging.

Finally, the alcohol is distilled off, the last traces being removed in an oven, so as to give an extract which consists of an aqueous solution of the various active substances. For cosmetological uses, the extract employed can be brought to the desired concentration by dilution, and, for example, an extract containing 40% of saponins can be obtained.

The two main active substances in this pilewort extract, namely the saponins and the phenolic acids, are identified by thin layer chromatography.

For the saponins, an acid hydrolysis is first carried out (10% hydrochloric acid is added and the mixture is then heated under reflux for 4 to 6 hours), followed by an extraction by the usual methods, and by dissolution in alcohol. The resulting alcoholic solution is chromatographed using chloroform, containing 5% of methanol, as the migration solvent, and a 10% strength solution of sulphuric acid as the developer, the material then being heated at 100° C for 10 minutes. Two purplish red spots appear at an Rf of about 0.20, corresponding to hederagenin, and at an Rf of 0.60, corresponding to oleanolic acid. These two genins are characteristic of the saponins.

For the phenolic acids, the chromatography is carried out directly on the pilewort extract, of which a portion is taken, treated with ethyl ether and redissolved in alcohol; a 90/25/4 mixture of benzene/dioxane/acetic acid is used as the migration solvent and UV light as the developer. Two fluorescent blue spots appear at Rf 0.55 and 0.65.

An example of carrying out the process is given below.

Tuberised pilewort roots, which have previously been dried so as to have a water content of about 10%, are ground until a powder having a mean particle size of between 0.2 and 0.6 mm is obtained.

40 kg of this powder are moistened with 40 l of 35°–45° C petroleum ether. After having left the powder and petroleum ether in contact for 4 to 5 hours, the extraction is carried out by adding 40 l of ether. The extraction takes place in the thimble of a percolator (Soxhlet), with a number of passes which is sufficient to dissolve almost all the products which are soluble in the 35°–45° C petroleum ether. At the end of the operation, the powder is dried so as to free it from any trace of solvent.

The powder is then brought into contact for 24 hours with 50 l of ethyl alcohol at 60°, after which 50 l of ethyl alcohol are added at 60° and the extraction is carried out at the boil in the same apparatus as that used for the extraction with ether. The coloured solution obtained is subjected to a first concentration so as to bring its alcoholic strength to about 20° to 30°.

After cooling to a temperature of between 5 and 10° C, the solution is filtered through asbestos discs so as to remove the impurities which have come out of solution. The solution filtered in this way is subjected to a second concentration so as to lower the alcoholic strength to about 10° to 15°. After cooling, a filtration is carried out as before.

Papaine is now added to the solution obtained, about 1 g of this enzyme being used per liter of solution. The enzyme is allowed to act for a period which must be at least several hours, though a period of treatment longer than this is not detrimental to the purification. The solution treated in this way is subjected to a concentration and, for this last concentration, it is preferred to use an oven with a hot air blower, the air temperature being between 30° and 60° C. Higher temperatures do not cause deterioration of the active principles if these temperatures are only maintained for a relatively short time.

Concentration is continued until the solids content is of the order of 40 to 50%. At least an equal volume of 96° strength ethyl alcohol is added to the viscous solution thus obtained, and the mixture is then left for at least 24 hours in a cold room.

At the end of this period of time, a more or less copious deposit forms which can be removed, as mentioned above, by filtration, centrifugation or decantation. The alcohol is then distilled off and the last traces are removed in an oven, and finally an aqueous extract containing all the active substances is obtained.

The extract thus obtained can be used in numerous cosmetic preparations, for example at concentrations of 0.5% to 6% of extract containing 40% of saponins. A typical such preparation is a sun cream having the following constituents:

| | |
|---|---|
| Fatty substances | 44.5 g |
| Solar radiation filter | 3.0 g |
| Preservative | 0.3 g |
| 3% strength "Carbopol 940" gel | 10.0 g |
| 40% strength pilewort extract | 1.0 g |
| Pure triethanolamine | 0.2 g |
| Distilled water | 40.0 g |
| Perfume | q.s. |

("Carbopol 940" is a tradename denoting a carboxyvinyl polymer).

The various contituents of the fatty phase are melted at 75° C, avoiding any local overheating, and the solar radiation filter is then added.

At the same time, the freshly distilled water is heated to 80° C, the preservative is added and the mixture is stirred until solution is complete; the 3% strength Carbopol 940 gel is then added and the mixture is stirred until a perfect dispersion in water is obtained, and lastly the 40% strength pilewort extract is added.

The aqueous phase at 80° C and the fatty phase at 75° C are then mixed in a mixer-homogeniser for 10 minutes. whilst maintaining the temperature at 75° C.

The triethanolamine, previously diluted with a little water, is now added and homogenisation is allowed to continue for a further 15 minutes at 75° C, after which the mixture is allowed to cool whilst stirring it gently.

When the temperature reaches 35° C, the perfume is added and the slow stirring is continued until ambient temperature is reached.

We claim:

1. A process for the extraction of the active substances from tuberised pilewort roots, said process comprising the following stages:
    a. macerating the pilewort roots, which have previously been dried and ground to a powder, in 35°–45° C petroleum ether, extracting them with this solvent, so as to remove all the substances soluble therein, separating the resulting solid residue from the solvent and drying it;
    b. macerating the dried residue in an aqeuous lower alcohol and extracting it with a supplementary amount of this aqueous alcohol;
    c. subjecting the resulting alcoholic extract to two successive concentrations in each of which the quantity of alcohol is approximately halved, allowing the extract to cool after each concentration, and removing precipitated impurities by filtration;
    d. treating the filtrate with papaine and concentrating it to a solids content of 40 to 50%;
    e. adding an equal volume of an aqueous lower alcohol to the viscous solution thus obtained, allowing the mixture to stand in the cold, and removing the insoluble products by decantation, filtration or centrifugation; and
    f. distilling off the alcohol so as to give an aqueous extract.

2. A process according to claim 1, wherein the aqueous lower alcohol used in stage (b) is methanol or ethanol of 70° to 50° strength.

3. A process according to claim 1, wherein in stage (a) 40 kg of powder are macerated in 40 l of 35°–45° C petroleum ether for several hours, and a further 40 l of 35°–45° C petroleum ether are added before effecting the extraction.

4. A process according to claim 1, wherein in stage (d) 1 l of the solution obtained in stage (c) is treated with 1 g of papaine.

5. A process according to claim 1, wherein in stage (c), after the treatment with papaine, ethanol or 90°–95° strength is added.

* * * * *